US00PP36646P3

(12) United States Plant Patent
Volz et al.

(10) Patent No.: US PP36,646 P3
(45) Date of Patent: May 6, 2025

(54) APPLE TREE NAMED 'HOT81A1'

(50) Latin Name: *Malus domestica*
Varietal Denomination: HOT81A1

(71) Applicants: The New Zealand Institute for Plant and Food Research Limited, Auckland (NZ); Institut De Recerca I Tecnologia Agroalimentaries (IRTA), Barcelona (ES); FruitFutur A.I.E, Lledia (ES)

(72) Inventors: Richard Volz, Havelock North (NZ); Cristian Fontich, Lleida (ES)

(73) Assignees: The New Zeeland Institute for Plant and Food Research Limited, Auckland (NZ); Institut De Recerca I Tecnlogia Agroalimentaries (IRTA), Barcelona (ES); FruitFutur A.I.E, Lleida (ES)

( * ) Notice: Subject to any disclaimer, the term of this patent is extended or adjusted under 35 U.S.C. 154(b) by 0 days.

(21) Appl. No.: 18/831,021

(22) Filed: May 1, 2024

(65) Prior Publication Data

US 2024/0373768 P1 Nov. 7, 2024

Related U.S. Application Data

(60) Provisional application No. 63/464,097, filed on May 4, 2023.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

(56) References Cited

U.S. PATENT DOCUMENTS

PP32,720 P2 * 1/2021 Bonany ..... A01H 1/106 Plt./161

OTHER PUBLICATIONS

U.S. Appl. No. 18/831,022, filed May 1, 2024.
U.S. Appl. No. 18/831,023, filed May 1, 2024.

* cited by examiner

*Primary Examiner* — Susan McCormick Ewoldt
*Assistant Examiner* — Zachariah Allan Kay
(74) *Attorney, Agent, or Firm* — LEYDIG, VOIT & MAYER, LTD.

(57) ABSTRACT

A new and distinct apple variety is described. The variety results from crossing the apple varieties 'A121R18T089' (not patented) and Gala 'Baigent' (U.S. Plant Pat. No. 4,121) in Havelock North, New Zealand. The fruit of the apple tree of this new variety have an appearance characterized by its dark red colour and creamy white background and it early harvest compared to other selections. This new variety has been named 'HOT81A1'.

3 Drawing Sheets

Genus and species plant named: *Malus domestica.*
Variety denomination: 'HOT81A1'.

BACKGROUND OF THE INVENTION

The new plant variety described herein resulted from a selection from a population of seedlings derived from the controlled crossing of the apple varieties 'A121R18T089' (not patented) (seed parent) and Gala 'Baigent' (U.S. Plant Pat. No. 4,121) (pollen parent). The planned cross was made in 2004 on trees located in Havelock North, Hawke's Bay, New Zealand and the seed transported and sown in plots in Gimenells near Lleida, Catalonia, Spain. 'HOT81A1' was selected in 2007 as a single plant from among a population of seedlings and was selected for its appearance, good flavor, texture and storage. It was asexually propagated first in Lleida, Spain by budding onto 'M9' (not patented), rootstock. The variety has since been observed over three asexually propagated generations and found to remain true to type.

SUMMARY OF THE INVENTION

'HOT81A1' is characterized by its fruit with good texture and flavor, harvesting late July to early August in Spain. Under growing conditions in Spain 'HOT81A1' is distinguished from other apple varieties due to the following unique characteristics: Compared to 'Baigent', 'HOT81A1' has an earlier harvest season by approximately 2 weeks, and a significantly higher proportion of the skin surface is covered by over color, 70-90%, compared to 'Baigent', 40-50%.

Under the growing conditions in Spain the new variety was able to be distinguished from its parents 'Baigent' and 'A121R18T089', by the following characteristics:

'Baigent': The time of harvest maturity is later than 'HOT81A1'.

'A121R18T089': 'HOT81A1' has a fruit skin overcolor pattern of a solid flush with weakly defined stripes; compared to 'A121R18T089' which has a solid flush overcolor pattern.

Asexual reproduction of this new variety by budding and grafting shows that the aforementioned characteristics are true to form and are established and transmitted through succeeding propagation. This is true of buds grafted onto M9 rootstocks.

BRIEF DESCRIPTION OF PHOTOGRAPHS

The accompanying photographs show typical specimens of the tree, foliage and fruit of the new variety as depicted in colours as nearly true as is reasonably possible to make the same in a colour illustration of this character.

DETAILED DESCRIPTION

Figure 1:
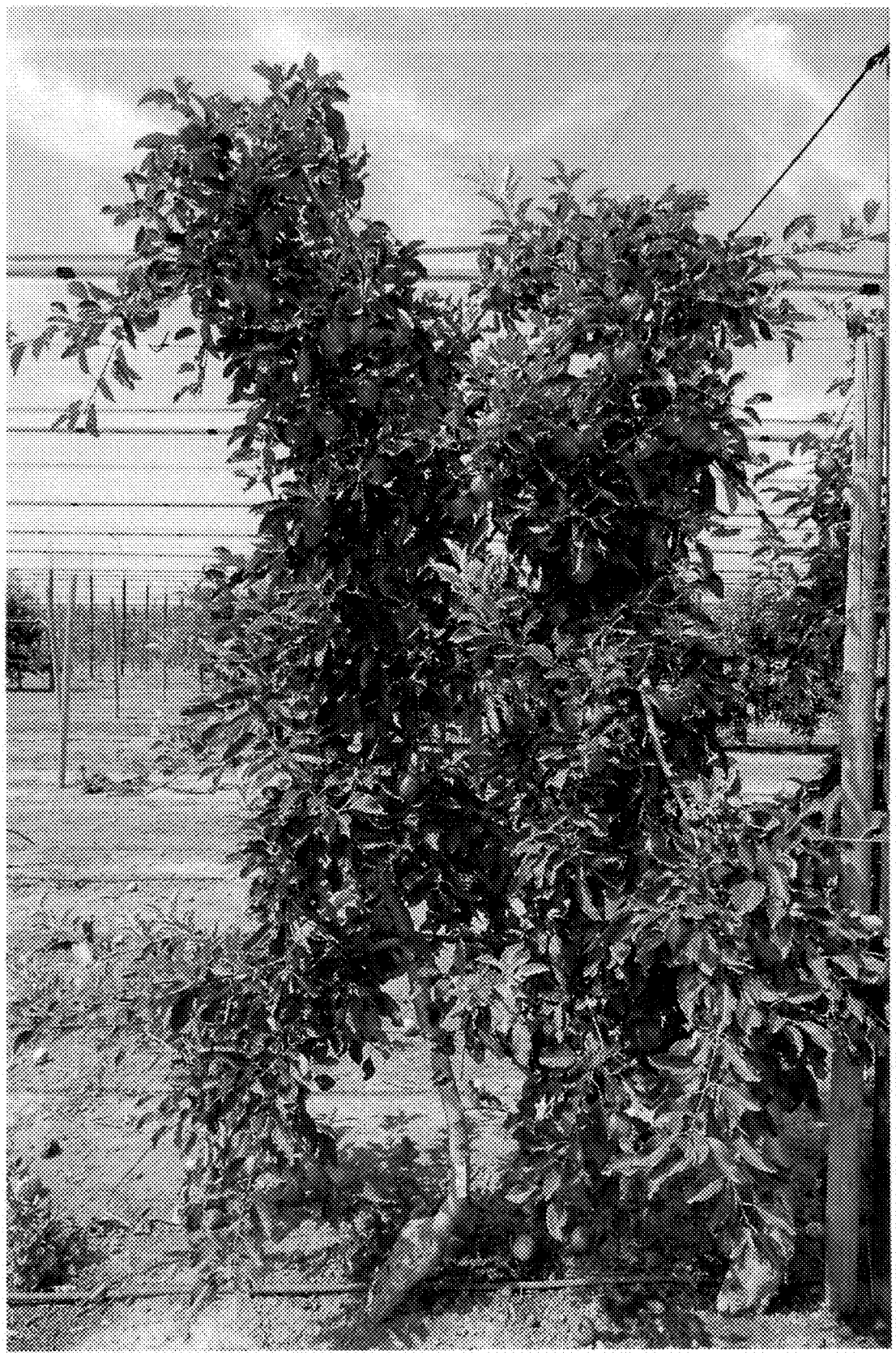
FIG. 1 shows a 3 year old tree of 'HOT81A1' scion on 'M9' rootstock in the field.
Figure 2:
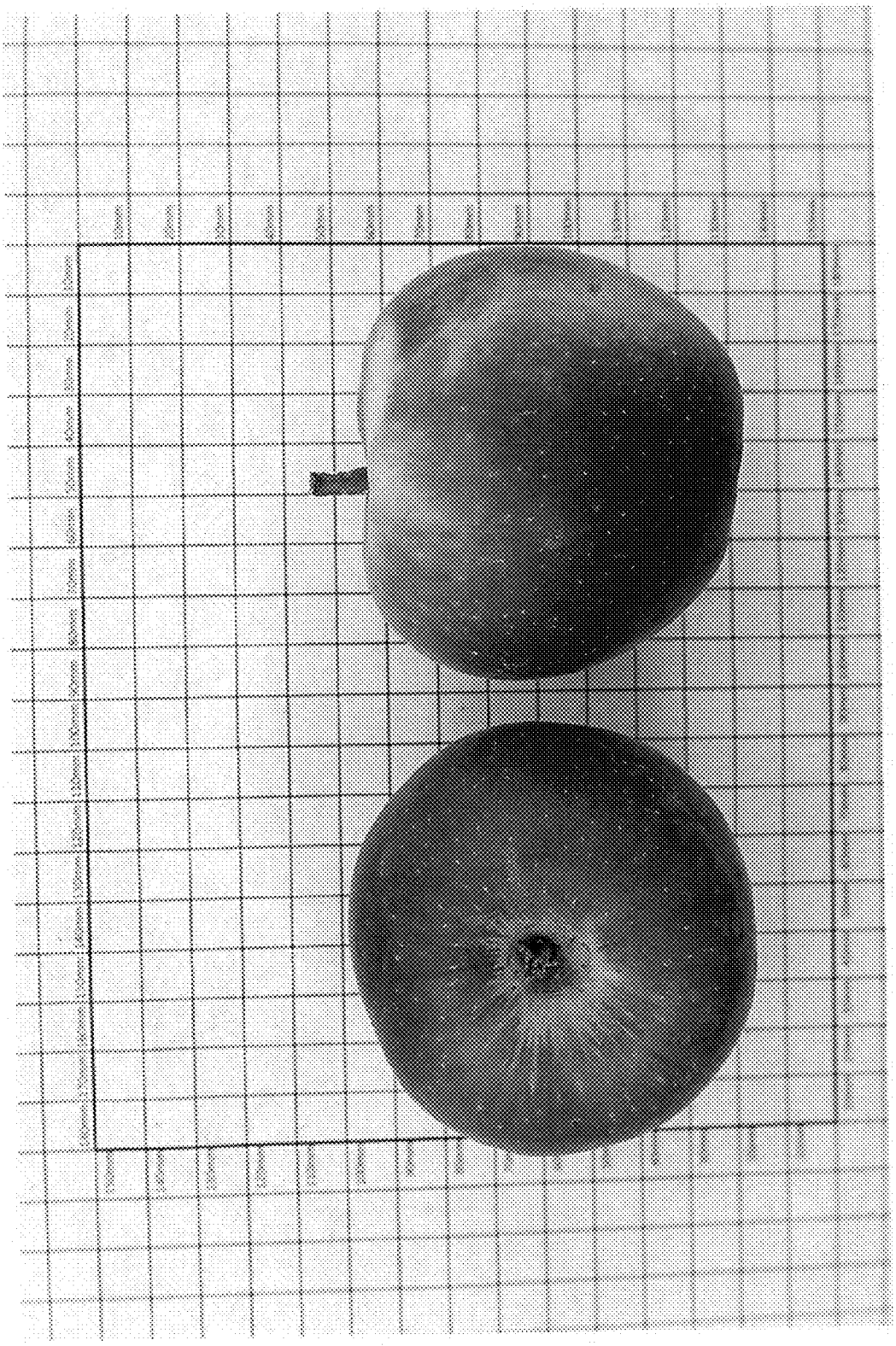
FIG. 2 shows whole 'HOT81A1' fruit.
Figure 3:
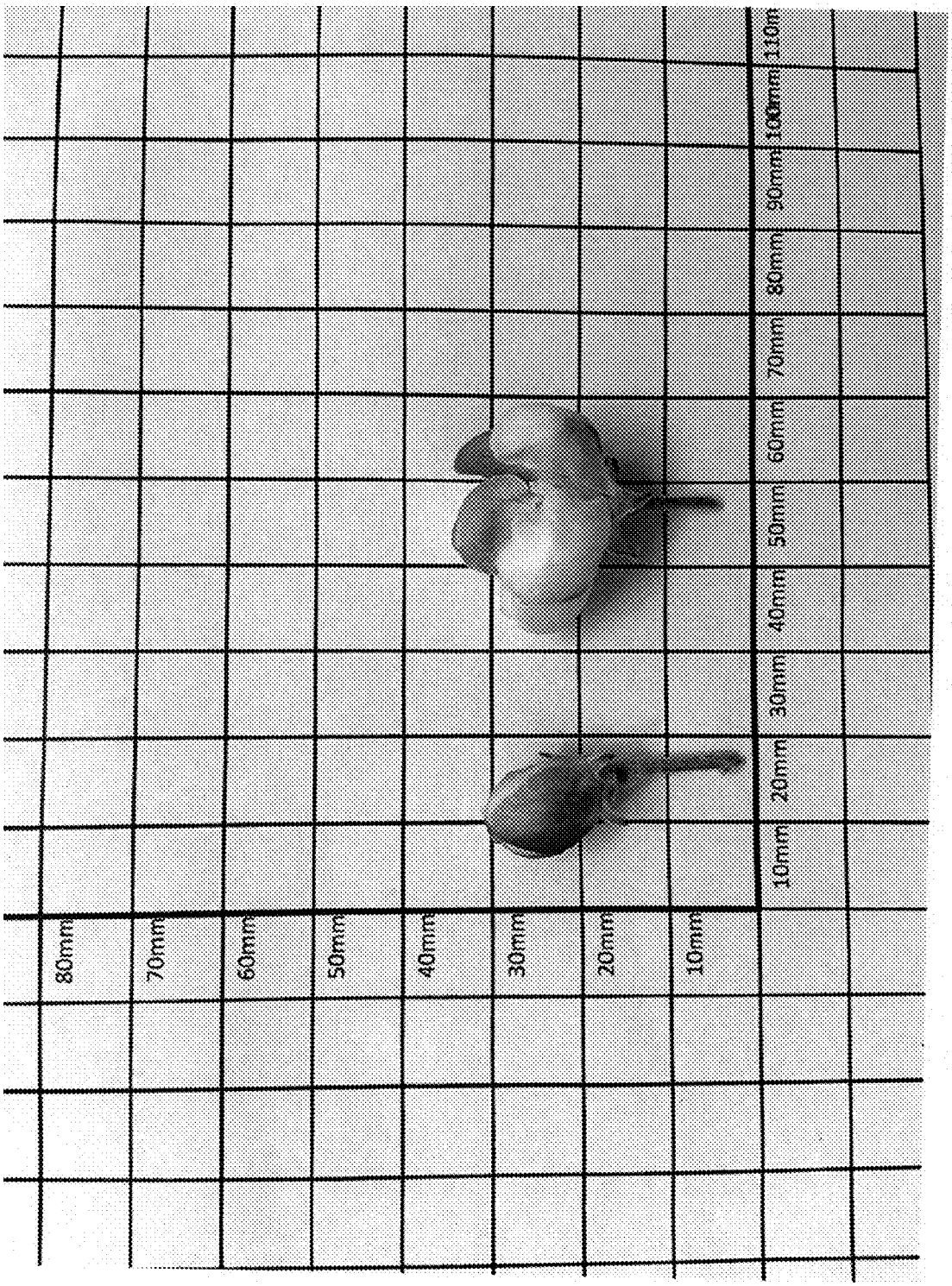
FIG. 3 shows 'HOT81A1' flower

The following is a description of the new variety with colour terminology in accordance with The Royal Horticultural Society Colour Charts (R.H.S.C.C.) sixth edition.

The specimens described were grown at Lleida, Catalonia, Spain. The observations were made over several seasons from 2014-2018 on 5-9 year old trees.

Tree: Ramified growth habit, approximately 3.46 m tall and 1.24 m wide; spreading habit; bearing on spurs and long shoots; on 'M9' rootstock, managed under standard orchard practice.

Trunk: Measurements were taken 20 cm from the graft union. Trunk circumference approximately 17.5 cm; colour dark greyish yellow 199D; bark texture both smooth and rough texture.

One year old shoot: Approximately 25.6 cm long, thin thickness with straight growth; colour on the sunny side greyish brown 166A; average internode length 3.68 cm; number of lenticels were sparse, elongated in shape and pale yellow 158B and approximately 0.62 mm in width and 1.7 mm in length.

Leaves: Average length 89.84 mm; average width 54.08 mm at the widest point; upper side of the blade greyish olive green NN137A; underside moderate yellow green 147B with weak pubescence; basal shape obtuse; apex shape right angled; margin of the leaves serrate; overall shape oval; the attitude in relation to the shoot upwards. Vegetative bud burst early March.

Petiole: Average length 26.93 mm; average width 1.93 mm; upperside colour moderate yellow green 147C; underside colour moderate yellow green 147C.

Stipule: Average length 6.06 mm; average width 0.44 mm; shape short and asymmetric; colour dark green 136A on the upper side; under side colour of the stipules moderate yellow green 147C.

Flowers: Colour at balloon stage moderate purplish red 59C; diameter of the open flower approximately 27.2 mm; petals were not touching, and there were six flowers per cluster; time of beginning of flowering late March, followed by full bloom on the approximately 6th April.

Petals: Five petals per flower with a rounded shape; average length 14.6 mm; average width 11.75 mm; with a truncated base; coloration light purple 77D with strong purplish red veins 72A.

Stamen: Average of 20 per flower. Filaments greenish white 155C and average length 8.56 mm. Anthers average length of 2.16 mm; average width 1.47 mm; colour light yellow 11B. Pollen colour brilliant greenish yellow 3A. Anther position below stigma.

Carpel: Average length 6.9 mm; exterior colour brilliant yellow green 149C.

Sepals: Five sepals per flower; overall shape of an acute and curved triangle; smooth margin; average length 5.4 mm; average width 2.9 mm; colour strong yellow green 144A.

Fruit size: Small; average width 68.31 mm; average height 58.27 mm; average weight 135.96 g.

Shape: Conic; position of maximum diameter slightly towards stalk; crowning at calyx end absent to weak. Eye basin average depth 12.196 mm; average width 23.17 mm.

Skin: Chewy texture; ribbing absent or weak; bloom of skin absent or weak; moderate; background colour light yellow 11B.

Overcolor: Approximately 80% of skin surface; moderate red 181A; pattern of overcolor flushed, striped and mottled width of stripes medium; large amount of russet around stalk cavity; amount of russet on cheeks absent or small; area of russet around eye basin absent or small.

Stalk: Average length 19.21 mm; average width 2.83 mm; curvature medium. Average depth of stalk cavity 13.446 mm; average width 28.274 mm.

Flesh: Medium, average fruit firmness 6.2 kgf; very juicy; greenish white 155C.

Flavor: Sweet; aroma sweet apple; soluble solids 13.1%.

Seeds: Five locules; medium seed size; average length 9.598 mm; average width 5.184 mm; colour moderate brown 200C.

Harvest: Late July—early August.

Use: Dessert. Adapted to hot climate growing conditions. Less sensitive to sunburn and cracking than 'Baigent'.

Keeping quality: Excellent, up to 6 months at 0.5° C.+1 week shelf life.

Pollination requirements: A suitable pollinator is required.

The invention claimed is:

1. A new and distinct variety of apple tree named 'HOT81A1' substantially as illustrated and described herein.

* * * * *